United States Patent
Nam et al.

(10) Patent No.: US 11,712,407 B2
(45) Date of Patent: Aug. 1, 2023

(54) HYBRID-TYPE MULTI-LAMELLAR NANOSTRUCTURE OF EPIDERMAL GROWTH FACTOR AND LIPOSOME AND METHOD FOR MANUFACTURING SAME

(71) Applicants: CELLTRION, INC., Incheon (KR); KOREA ADVANCED INSTITUTE OF SCIENCE AND TECHNOLOGY, Daejeon (KR)

(72) Inventors: Yoon Sung Nam, Daejeon (KR); Sung Duk Jo, Seoul (KR); Bon Il Koo, Daejeon (KR)

(73) Assignees: CELLTRION, INC., Incheon (KR); Korea Advanced institute of Science and Technology, Daejeon (KR)

( * ) Notice: Subject to any disclaimer, the term of this patent is extended or adjusted under 35 U.S.C. 154(b) by 0 days.

(21) Appl. No.: 15/540,344

(22) PCT Filed: Dec. 30, 2015

(86) PCT No.: PCT/KR2015/014504
§ 371 (c)(1),
(2) Date: Jan. 29, 2018

(87) PCT Pub. No.: WO2016/108634
PCT Pub. Date: Jul. 7, 2016

(65) Prior Publication Data
US 2018/0161254 A1    Jun. 14, 2018

(30) Foreign Application Priority Data
Dec. 30, 2014  (KR) .................. 10-2014-0193921

(51) Int. Cl.
*A61K 8/14*    (2006.01)
*A61Q 19/00*    (2006.01)
(Continued)

(52) U.S. Cl.
CPC ............... *A61K 8/14* (2013.01); *A61K 8/553* (2013.01); *A61K 8/64* (2013.01); *A61K 9/0014* (2013.01);
(Continued)

(58) Field of Classification Search
CPC .......... A61K 9/127; A61K 8/14; A61K 8/553; A61K 9/0014; A61K 9/1272; A61K 8/64;
(Continued)

(56) References Cited

U.S. PATENT DOCUMENTS

| 5,358,706 A | 10/1994 | Marlin et al. |
| 2006/0172003 A1* | 8/2006 | Meers ................. A61K 9/1271 424/450 |

(Continued)

FOREIGN PATENT DOCUMENTS

| CN | 1180697 A | 5/1998 |
| CN | 1312707 A | 9/2001 |

(Continued)

OTHER PUBLICATIONS

Bunuales, M. et al in Nanomedicine (Lond), vol. 6 (1), pp. 89-98, Jan. 2011.*

(Continued)

*Primary Examiner* — Gollamudi S Kishore
(74) *Attorney, Agent, or Firm* — MaxGoLaw PLLC

(57) ABSTRACT

The present invention relates to a hybrid-type multi-lamellar nanostructure of an epidermal growth factor and a liposome and a method for manufacturing same. The new type of hybrid-type multi-lamellar nanostructure not only has a high epidermal growth factor encapsulating efficiency, but also can be manufactured through a simple process, such that the same can be easily delivered into a living body or a cell while maintaining a high physiological activity of the epidermal growth factor.

3 Claims, 5 Drawing Sheets

(51) Int. Cl.
| | |
|---|---|
| *A61K 8/55* | (2006.01) |
| *A61Q 19/08* | (2006.01) |
| *A61K 9/00* | (2006.01) |
| *A61K 9/127* | (2006.01) |
| *A61K 8/64* | (2006.01) |

(52) U.S. Cl.
CPC ............ *A61K 9/127* (2013.01); *A61K 9/1272* (2013.01); *A61Q 19/00* (2013.01); *A61Q 19/08* (2013.01); *A61K 2800/56* (2013.01)

(58) Field of Classification Search
CPC .... A61K 2800/56; A61Q 19/08; A61Q 19/00; A61P 17/00
See application file for complete search history.

(56) References Cited

U.S. PATENT DOCUMENTS

| | | | |
|---|---|---|---|
| 2008/0138394 A1* | 6/2008 | Kim | A61P 31/20 424/450 |
| 2010/0008885 A1 | 1/2010 | Daly et al. | |
| 2012/0135065 A1* | 5/2012 | Panzner | A61K 9/1272 424/450 |
| 2013/0142866 A1* | 6/2013 | Theisinger | A01N 1/0221 424/450 |
| 2014/0056970 A1* | 2/2014 | Panzner | A61K 31/7088 424/450 |
| 2015/0182590 A1* | 7/2015 | Santana Milian | A61K 9/0014 424/450 |

FOREIGN PATENT DOCUMENTS

| | | | |
|---|---|---|---|
| CU | 2012-0112 | * | 3/2014 |
| EP | 0590655 A1 | | 4/1994 |
| EP | 0711148 B1 | | 5/1996 |
| ES | 2325901 A1 | | 9/2009 |
| JP | H06192130 A | | 7/1994 |
| JP | H10152461 A | | 6/1998 |
| JP | 2009191004 A | | 8/2009 |
| JP | 2009234945 A | | 10/2009 |
| KR | 100752990 | | 8/2007 |
| KR | 20080106618 A | | 12/2008 |
| KR | 100962566 | | 6/2010 |
| KR | 100986604 B1 | | 10/2010 |
| KR | 20110076068 A | | 7/2011 |
| WO | 9503787 A1 | | 2/1995 |
| WO | 9965465 A1 | | 12/1999 |
| WO | 2005042570 A1 | | 5/2005 |

OTHER PUBLICATIONS

Kikuchi, A., et al. BBRC, vol. 227, pp. 666-671, 1996.*

Bangham, A.D., Standish, M.M., Watkins, J.C., "Diffusion of Univalent Ions Across the Lamellae of Swollen Phospholipids", Journal of Molecular Biology (1965), pp. 238-252, vol. 13.

Radler, Joachim O., Koltover, Ilya, Salditt, Tim, Safinya, Cyrus R., "Structure of DNA-Cationic Liposome Complexes: DNA Intercalation in Multilamellar Membranes in Distinct Interhelical Packing Regimes", Science, Feb. 7, 1997, pp. 810-814, vol. 275, http://www.sciencemag.org.

Torchilin, Vladimir P., "Recent Advances with Liposomes as Pharmaceutical Carriers", Nat. Rev. Drug Discov., Feb. 2005, pp. 145-160, vol. 4.

Martins, Susana, Sarmento, Bruno, Ferreira, Domingos C., Souto, Eliana B., "Lipid-Based Colloidal Carriers for Peptide and Protein Delivery—Liposomes Versus Lipid Nanoparticles", International Journal of Nanomedicine (2007), pp. 595-607, vol. 2, issue 4, Dove Medical Press Limited (2007).

Pisal, Dipak S., Kosloski, Matthew P., Balu-Iyer, Sathy V., "Delivery of Therapeutic Proteins", J. Pharm. Sci., Jun. 2010, pp. 2557-2575, vol. 99, issue 6, J. Pharm. Sci. Author manuscript; available in PMC Jun. 1, 2011.

Amenitsch, H. et al., "Existence of hybrid structures in cationic liposome/DNA complexes revealed by their interaction with plasma proteins", Colloids and Surfaces B: Biointerfaces, 2011 (Available online: Aug. 26, 2010), pp. 141-146, vol. 82, © 2010 Elsevier B.V.; DOI: 10.1016/j.colsurfb.2010.08.030.

English translation of Japanese Notification of Reasons for Refusal dated May 8, 2018 for Japanese Application No. 2017-534268 filed Dec. 30, 2015.

Supplementary European Search Report dated Jun. 6, 2018 for European Application No. 15875728, filed Dec. 30, 2015.

Alemdaroglu, Ceren, et al., "Investigation of Epidermal Growth Factor Containing Liposome Formulation Effects on Burn Wound Healing", Journal of Biomedical Materials Research Part A, Oct. 15, 2007, pp. 271-283, vol. 85A, issue 1, Copyright Wiley Periodicals, Inc. (2007); DOI: 10.1002/jbm.a.31588.

CN1180697A machine translation.
EP0711148B1 abstract.
CN1312707A abstract.

Zhou Yu-dan et al., Cationic Liposome Used as Gene VectorMaterials and Preparation Techniques.

CN OA of Aug. 22, 2019.
CN OA of Aug. 22, 2019 English.
CN OA search report.

Kyoung Mi Kim, et al., "New Cationic Liposome with Enhanced Stability and Transfection Efficiency for Gene Delivery," J. Kor. Pharm. Sci, vol. 28, No. 2 (1998), pp. 93-98.

Bon Il Koo, et al., "Protein-induced metamorphosis of unilamellar lipid vesicles to multilamallar hybrid vesicles," Journal of Controlled Release 331 (2021), pp. 187-197.

Ricardo Gaspar, et al., "Lipid-Nucleic Acid Complexes: Physicochemical Aspects and Prospects for Cancer Treatment," Molecules 2020, 25, 5006.

* cited by examiner

HYBRID-TYPE MULTI-LAMELLAR NANOSTRUCTURE OF EPIDERMAL GROWTH FACTOR AND LIPOSOME AND METHOD FOR MANUFACTURING SAME

TECHNICAL FIELD

The present invention relates to a hybrid-type multi-lamellar nanostructure of an epidermal growth factor (EGF) and a liposome and a method for manufacturing same. More specifically, the present invention relates to a novel protein-lipid hybrid-type multi-lamellar nanostructure made by multivalent electrostatic interactions in addition to hydrophobic interactions between empty vesicles formed of cationic lipid and anionic epidermal growth factor protein as well as a method for manufacturing same.

BACKGROUND ART

As interest in beauty has increased, physiologically active proteins having a specific mechanism of action and good efficacy have attracted as materials for functional cosmetic products. However, physiologically active proteins do not easily permeate the skin, due to their high molecular weight, short half-life and structural unstability. For this reason, interest in skin delivery of these physiologically active proteins has rapidly increased.

Among physiologically active proteins, epidermal growth factor is known to play a key role in skin regeneration, and thus is being used as a functional cosmetic component. Epidermal growth factor is currently listed in the US Cosmetic, Toiletry, and Fragrance Association (CTFA)'s international Cosmetic ingredient Dictionary (ICID) and was also approved by the Korean Ministry of Food and Drug Safety (MDFS) for use as a cosmetic raw material, and thus has been formally used as a cosmetic raw material in South Korea and other countries (Korea Food and Drug Administration Notification No. 2006-12 (Apr. 12, 2006)).

However, the biggest problem in skin delivery of physiologically active protein components such as epidermal growth factor is that these protein components have low skin absorption rates (permeation rates). A typical method to overcome this problem is to deliver physiologically active proteins such as epidermal growth factors into the skin by use of liposomes as carriers. Liposomes are lipid bilayer vesicles formed mainly of amphipathic phospholipid that is a component of the cell membrane. A hydrophilic substance may be encapsulated in the internal aqueous compartment of the liposome, or a hydrophobic substance may be loaded in the lipid bilayer. The layer structure of the liposome is similar to the structure of the cell membrane, and thus the liposome has low toxicity and can deliver a substance by fusion with the cells or by endocytosis. Particularly, because the liposome has excellent biocompatibility, studies on the use of the liposome as a carrier have been actively conducted (Bangham, A. D.; Torchilin, V. P., 2005, Nat. Rev. Drug Discov., 4: 145).

Despite such advantages, the liposome is difficult to use widely, due to several problems. One of the problems of the liposome is that the efficiency of encapsulation in the liposome is low. Particularly, a hydrophilic substance can be encapsulated in only the internal aqueous compartment of the liposome, and also the efficiency of encapsulation will necessarily be low, because the volume of the internal aqueous compartment is small. It generally shows an encapsulation efficiency of about 10-20%, and shows a serious technical limitation because the amount of protein encapsulated is very low relative to the total weight of the liposome (Martins, Susana et al, 2007, Int. J. Nanomed., 2. 4,595). On the other hand, a lipophilic substance is encapsulated with a relatively high efficiency, because it is solubilized in the lipid bilayer. However, in some cases, the lipophilic substance can unstabilize the lipid bilayer to reduce the stability of the liposome. Thus, the liposome technology is commercially applied to some lipophilic substances, but the use thereof for hydrophilic substances is very insignificant.

Another problem in the use of liposomes as a protein delivery carrier is that a physiologically active protein is severely denatured in a general liposome preparation process to lose its characteristic physiological activity. As a general liposome preparation method, the Bangham method (Bangham et. al., 1965 J. Mol. Biol. 13:28-252) or the high-pressure homogenization method is widely used. The Bangham method comprises: adding and dissolving a surfactant in a solvent in a class device; evaporating the solution to form a surfactant (i.e., phospholipid) layer on the glass wall; introducing a material solution to be encapsulated; and intensively stirring or ultrasonically homogenizing the solution, thereby preparing a liposome. In the high-pressure homogenization method, liposome components are mixed with each other and passed through a cartridge cell or valve (also called "interaction chamber") having micro-pores of sub-micron size. Herein, the size of the micro-pores is about 50-300 μm. By great shear stress that occurs during the passage, a lipid bilayer made of a surfactant is formed, and a drug is encapsulated in the phospholipid bilayer. If a physiologically active protein is trapped using these methods, the protein can be aggregated, denatured, oxidized or degraded due to its exposure to severe conditions such as high pressure, high temperature, frictional heat caused by shear stress in the micro-pores, and the use of an organic solvent, and thus is highly likely to lose its characteristic physiological activity.

For example, Korean Patent No. 0752990 relates to a nanoliposome composed of a liposome layer comprising esterified lecithin that is neutral lipid, and it discloses a composition for prevention or treatment of skin disease, comprising: the nanoliposome having epidermal growth factor encapsulated therein; and a natural extract having anti-inflammatory activity. Korean Patent No. 0962566 discloses a nanoliposome containing human growth hormone as an active ingredient, in which the nanoliposome is produced by a high-pressure homogenization method using soybean lecithin that is neutral lipid. However, the physiologically active protein-containing liposomes disclosed in the above-described patent documents have problems in that the efficiency of encapsulation of the active ingredient is very low and in that the physiological activity of the protein is severely reduced because the liposomes are produced at high temperature and high pressure.

Thus, it is required to develop a method capable of ensuring high encapsulation rate while stably maintaining the physiological activity of epidermal growth factor in a process of preparing a carrier structure. According to the analysis of previous study results, there were many attempts to use various additives or develop new process methods in order to increase the efficiency with which physiologically active proteins such as epidermal growth factor are encapsulated in the internal aqueous compartment of liposomes (Pisal, Dipak S. et al, 2010, J. Pharm. Sci., 99.6, 2557-2575). However, all the attempts are characterized in that they are focused on increasing the efficiency with which proteins are encapsulated in the internal aqueous compartment of liposomes.

DISCLOSURE

Technical Problem

Accordingly, the present inventors have made efforts to develop a new approach method capable of efficiently incorporating or trapping epidermal growth factor in liposomes while the high physiological activity of epidermal growth factor. Particularly, thinking out of the box of approaches that encapsulate protein in the internal aqueous compartment of liposomes, the present inventors have conducted studies on a method of producing new nanostructures by inducing more positive interactions between liposomes and protein. Particularly, the present inventors have paid attention to the study indicating that nucleic acid that is an anionic biopolymer is conjugated with cationic liposomes to form new nanostructures (Safinya, C. R. at al, 1997, Science, 275.5301, 810-814), and thus the present inventors have conducted studies on a method which does not encapsulate protein in a liposome preparation process, but makes new structures through liposome-protein interactions after preparation of the liposomes. As a result, the present inventors have found that, when a combination between multivalent electrostatic interactions and hydrophobic interactions between empty vesicles formed of cationic lipid and epidermal growth factor that is an anionic protein is used under suitable conditions, a new type of protein-lipid hybrid-type multi-lamellar nanostructures in which the epidermal growth factor was trapped with a very high efficiency while maintaining its physiological activity can be prepared, thereby completing the present invention.

Technical Solution

Therefore, one of the objects of the present invention is to provide a hybrid-type multi-lamellar nanostructure made by interactions between epidermal growth factor and empty vesicles formed of cationic lipid.

Another object of the present invention is to provide a method of manufacturing a protein-lipid hybrid-type multi-lamellar nanostructure by a spontaneous self-assembly process occurring at normal temperature and normal pressure by mixing epidermal growth factor and empty vesicles formed of cationic lipid.

Still another object of the present invention is to provide a cosmetic composition containing the hybrid-type multi-lamellar nanostructure.

Advantageous Effects

The novel hybrid-type multi-lamellar nanostructure according to the present invention not only exhibits high encapsulation efficiency but also simple process for manufacturing same, thereby allows an epidermal growth factor to be delivered into the body or cells with high physiological activity.

BEST MODE

Figure 1:
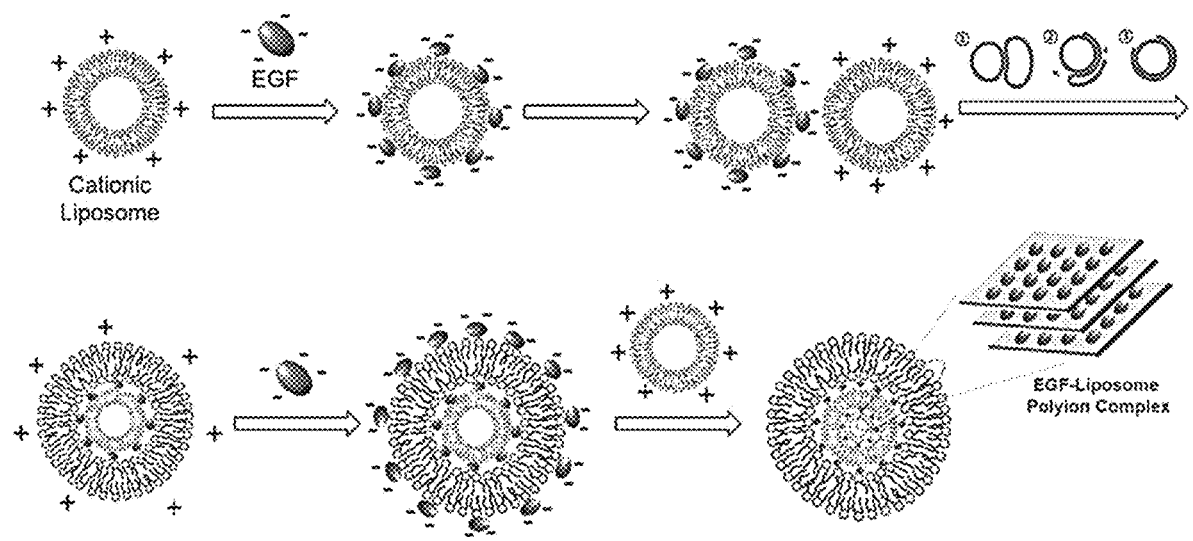
FIG. 1 is a schematic view showing a process of forming EGF-DOTAP hybrid-type multi-lamellar nanostructures according to one embodiment of the present invention.

The present invention provides a hybrid-type multi-lamellar nanostructure formed by interactions between epidermal growth factor and empty vesicles formed of cationic lipid; a method of manufacturing a protein-lipid hybrid-type multi-lamellar nanostructure by self-assembly between epidermal growth factor and empty vesicles formed of cationic lipid; and a cosmetic composition containing the hybrid-type multi-lamellar nanostructure.

Hereinafter, the present invention is described in detail.

The present invention relates to an epidermal growth factor-liposome hybrid-type multi-lamellar nanostructure, comprising:

(a) an empty unilamellar liposome composed of a cationic lipid bilayer;

(b) one or more unilamellar liposomes surrounding the empty unilamellar liposome and composed of a cationic lipid bilayer; and (c) an epidermal growth factor, wherein the epidermal growth factor is associated with the unilamellar liposomes by electrostatic interaction and located between the unilamellar liposomes.

The cationic lipid may be one or more selected from the group consisting of 1,2-diolecyl-sn-glycero-3-ethylphosphocholine (EDOPC), 1-palmitoyl-2-oleoyl-sn-glycero-3-ethylphosphocholine (EPOPC), 1,2-dimyristoyl-sn-glycero-3-ethylphosphocholine (EDMPC), 1,2-distearoyl-sn-glycero-3-ethylphosphocholine (SPC), 1,2-dipalmitoyl-sn-glycero-3-ethylphosphocholine (EDPPC), 1,2-dioleoyl-3-trimethylammonium-propane (DOTAP), N-[1-(2,3-dioleyloxy)propyl]-N,N,N-trimethylammonium chloride (DOTMA), 3β-[N-(N',N'-dimethylaminoethane)-carbamoyl]cholesterol (DC-cholesterol), dioleoyl glutamide, distearoyl glutamide, dipalmitoyl glutamide, dioleoyl aspartamide, and dimethyldioctadecylammonium bromide (DDAB), but is not limited thereto.

The empty unilamellar liposome may have a zeta potential (or surface charge) of +1 to 100 mV, preferably +30 mV or more.

The hybrid-type multi-lamellar nanostructure may have a particle size of 50-900 nm, preferably 50-500 nm, more preferably 100-200 nm. If the particle size of the nanostructure is greater than 900 nm, the nanostructure will be difficult to permeate the skin, due to its large size, and thus will be unsuitable for delivering the epidermal growth factor into the skin. If the particle size of the nanostructure is smaller than 50 nm, a problem may arise in terms of safety, because the safety of the nanostructure for the human body has not been proven.

The epidermal growth factor:cationic lipid weight ratio (w/w) of the hybrid-type multi-lamellar nanostructure may be 0.001 to 2.5:1, preferably 0.001 to 2.3:1, more preferably 0.001 to 2.0:1. If the epidermal growth factor:cationic lipid weight ratio (w/w) is less than 0.001:1, the multi-lamellar nanostructure cannot be formed. If the epidermal growth factor:cationic lipid weight ratio (w/w) is more than 2.5:1, the nanostructure will be difficult to penetrate the skin, due to its large size, and thus will be unsuitable for delivering the epidermal growth factor into the skin.

The encapsulation rate of the epidermal growth factor in the hybrid-type multi-lamellar nanostructure may be at least 60%, preferably at least 80%, more preferably at least 90%.

The epidermal growth factor that is used in the present invention may be a recombinant protein prepared by Celltrion, Inc. (Korea), or may be a commercially available product.

The "hybrid-type multi-lamellar nanostructure" according to the present invention is a novel nanostructure formed by multivalent electrostatic and hydrophobic interactions between empty vesicles formed of cationic lipid and anionic epidermal growth factor. More specifically, as shown in FIG. 1, a new type of hybrid-type multi-lamellar nanostructures may be formed by spontaneous self-assembly between empty vesicles and epidermal growth factor.

As used herein, the term "an empty vesicle" refers to a vesicle having an empty internal space. More specifically, the term means a general liposome composed of a lipid bilayer. Even more specifically, the term "an empty vesicle" means an empty unilamellar liposome in the present invention.

"One or more unilamellar liposomes" according to the present invention may be multivesicular liposomes (MVLs) having multiple non-concentric internal aqueous compartments in the liposome particle, or multivesicular liposomes (MVLs) having a series or substantially spherical shells formed of lipid bilayers interspersed with aqueous layers, but are not limited thereto.

The present invention also relates to a method for preparing hybrid-type multi-lamellar nanostructures, comprising the steps of:

(1) preparing a solution containing an empty unilamellar liposome with a uniform particle size composed of a cationic lipid;

(2) preparing an aqueous solution containing an epidermal growth factor; and (3) mixing the empty unilamellar liposome-containing solution, obtained in step (1), with the epidermal growth factor-containing aqueous solution obtained in step (2).

The cationic lipid in step (1) may be one or more selected from the group consisting of 1,2-dioleoyl-sn-glycero-3-ethylphosphocholine (EPOPC), 1-palmitoyl-2-oleoyl-sn-glycero-3-ethylphosphocholine (EPOPC), 1,2-dimyristoyl-sn-glycero-3-ethylphosphocholine (EDMPC), 1,2-distearoyl-sn-glycero-3-ethylphosphocholine (SPC), 1,2-dipalmitoyl-sn-glycero-3-ethylphosphocholine (EDPPC), 1,2-dioleoyl-3-trimethylammonium-propane (DOTAP), N-[1-(2,3-dioleyloxy)propyl]-N,N,N-trimethylammonium chloride (DOTMA), 3β-[N-(N',N'-dimethylaminoethane)-carbamoyl]cholesterol (DC-cholesterol), dioleoyl glutamide, distearoyl glutamide, dipalmitoyl glutamide, dioleoyl aspartamide, and dimethyldioctadecylammonium bromide (DDAB), but is not limited thereto.

The empty unilamellar liposomes in step (1) may be prepared by a general liposome preparation method. The liposome preparation method may be selected from the group consisting of a Bangham method, a dry lipid hydration method, a freeze and thawing method in which a process of freezing with liquid nitrogen followed by thawing at room temperature is repeated, an extrusion method, a sonication method, and a microfluidizer method, but is not limited thereto.

The empty unilamellar liposome obtained in step (1) may have a particle size of 100-300 nm, preferably 100-250 nm, more preferably 100-200 nm.

Figure 5:
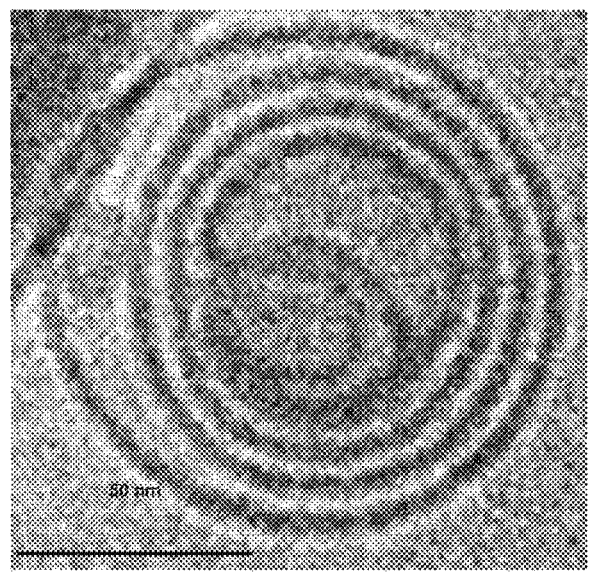
FIG. 5 shows the actual structure of EGF-DOTAP hybrid-type multi-lamellar nanostructures prepared according to one embodiment of the present invention observed by cryo-TEM.

In step (3), the epidermal growth factor and the empty unilamellar liposomes are associated with each other by multivalent electrostatic and hydrophobic interactions therebetween to form novel protein-lipid hybrid-type multi-lamellar nanostructures. More specifically, as shown in FIG. 1, the empty unilamellar liposomes and the epidermal growth factor are spontaneously self-assembled by multivalent electrostatic and hydrophobic interactions therebetween, thus forming hybrid-type multi-lamellar nanostructures as shown in FIG. 5.

The hybrid-type multi-lamellar nanostructure comprises:

(a) an empty unilamellar liposome composed of a cationic lipid bilayer;

(b) one or more unilamellar liposomes surrounding the empty unilamellar liposome and composed of a cationic lipid bilayer; and (c) an epidermal growth factor, wherein the epidermal growth factor is located between the unilamellar liposomes.

The hybrid-type multi-lamellar nanostructures may have a Particle size of 50-900 nm, preferably 50-500 nm, more preferably 100-200 nm.

The epidermal growth factor: cationic lipid weight ratio (w/w) of the hybrid-type multi-lamellar nanostructure may be 0.001 to 2.5:1, preferably 0.001 to 2.3:1, more preferably 0.001 to 2.0:1.

The encapsulation rate of the epidermal growth factor in the hybrid-type multi-lamellar nanostructure may be at least 60%, preferably at least 80%, more preferably at least 90%.

Unlike a general process for preparing liposome, the preparation method according to the present invention comprises preparing empty lipid vesicles (empty unilamellar liposomes) having a desired size and mixing the prepared liposomes with a physiologically active component. Accordingly, the preparation method according to the present invention has an advantage in that a process in which the epidermal growth factor (that is a physiologically active component) is exposed to high pressure, high temperature or a strong acidic solution during liposome preparation is omitted, and thus the physiological activity of the epidermal growth factor can be maintained.

The present invention also relates to a cosmetic composition containing the hybrid-type multi-lamellar nanostructure.

The hybrid-type multi-lamellar nanostructure can permeate to the dermis of the skin, but is not limited thereto.

The type of cosmetic composition according to the present invention is not particularly limited, and the cosmetic composition of the present invention may contain cosmetic composition components that are generally used in the art to which the present invention, depending on the formulation to be prepared. The cosmetic composition of the present invention may be prepared as formulations, including skin softener, emulsion, nourishing cream, pack, beauty liquid, essence, and the like, and may further contain one or more selected from among oils, water, surfactants, moisturizing agents, lower alcohols, thickeners, chelating agents, pigments, preservatives, fragrances and the like, depending on the formulation to be prepared.

MODE FOR INVENTION

Hereinafter, the present invention will be described in further detail with reference to examples, experimental examples and formulation examples. It is to be understood, however, that these examples, experimental examples and formulation examples are for illustrative purposes only and are not intended to limit the scope of the present invention.

EXAMPLE 1

Preparation of EGF-DOTAP Hybrid-Type Multi-Lamellar Nanostructures 1.1: Preparation of Cationic Empty Unilamellar Liposomes Containing DOTAP The cationic lipid DOTAP (20.96 mg, Avanti Polar Lipid, Inc.) was dissolved in 1 ml of chloroform, and then mixed in a round glass flask. In a rotary evaporator, nitrogen was flushed into the lipid solution at low rate to remove the chloroform, and the lipid was dried, thereby forming a thin lipid layer. The formed lipid layer was further dried in a vacuum for 12 hours to completely remove the remaining chloroform. 1 ml of purified water was added to the prepared lipid layer, followed by stirring at 37° C. for 2 hours, thereby preparing empty lipid vesicles. The obtained empty lipid vesicles were extruded several times through a polycarbonate membrane (Avanti Polar Lipid, Inc.) having a pore size 100 nm, thereby preparing cationic empty unilamellar liposomes comprising DOTAP and having a uniform particle size.

1.2: Preparation of EGF-DOTAP Hybrid-Type Multi-Lamellar Nanostructures

A solution (500 µl) containing the cationic empty unilamellar liposomes comprising DOTAP, prepared in Example 1.1, and an EGF solution (500 µl, Celltrion, Inc.), were mixed with each other on purified water at normal temperature, thereby preparing EGF-DOTAP hybrid-type multi-lamellar nanostructures. The prepared nanostructures were stored at 4° C. until use.

Experimental Example 1

Evaluation of Formation of EGF-DOTAP Hybrid-Type Multi-Lamellar Nanostructures 1.1: Confirmation of Formation of Cationic Empty Unilamellar Liposomes The particle size and zeta potential of the cationic empty unilamellar liposomes prepared in Example 1.1 were measured using dynamic light scattering (DLS, ELSZ-1000, Otsuka Electronics), and the results of the measurement are shown in Table 1 below. The measurement results indicated that the prepared cationic empty unilamellar liposomes had a particle size of 200 nm and a positive surface charge.

TABLE 1

| Empty unilamellar liposomes | | |
|---|---|---|
| Empty unilamellar liposomes | Particle size (nm) | Zeta potential (mV) |
| DOTAP | 197.7 ± 4.9 | 56.5 ± 2.5 |

1.2: Confirmation of Formation of EGF-DOTAP Hybrid-Type Multi-Lamellar Nanostructures The particle size and zeta potential of the EGF-DOTAP hybrid-type multi-lamellar nanostructures prepared in Example 1.2 were measured using DLS, and the transmittance thereof was measured at 500 nm using a spectrophotometer (Jasco-815, Jasco. Inc.). The results of the measurement are shown in FIGS. 2 and 3.

Figure 2:
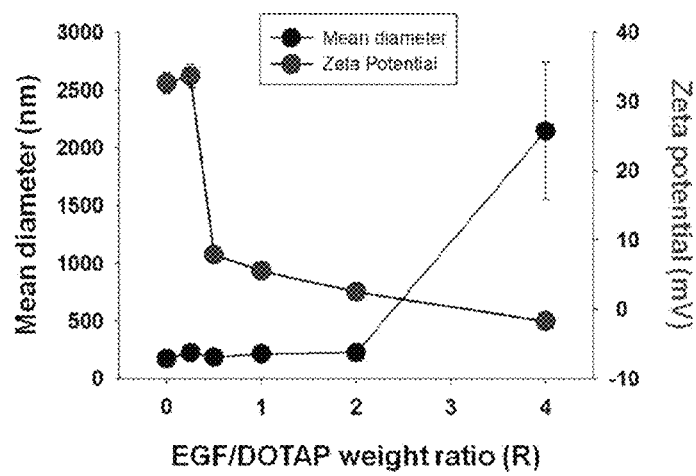
FIG. 2 shows the results of measuring the particle size and surface charge of EGF-DOTAP hybrid-type multi-lamellar nanostructures prepared according to one embodiment of the present invention.

As can be seen in FIG. 2, when the EGF/DOTAP weight ratio was 2 or less, the particle size of the EGF-DOTAP hybrid-type multi-lamellar nanostructures was about 200 nm, which is similar to the particle size of the DOTAP empty unilamellar liposomes, whereas the surface charge of the EGF-DOTAP hybrid-type multi-lamellar nanostructures decreased compared to that of the empty unilamellar liposomes. This is believed to be because the anionic EGF is associated with the cationic empty unilamellar liposomes by electrostatic interactions to thereby form a new type of structures.

Figure 3:
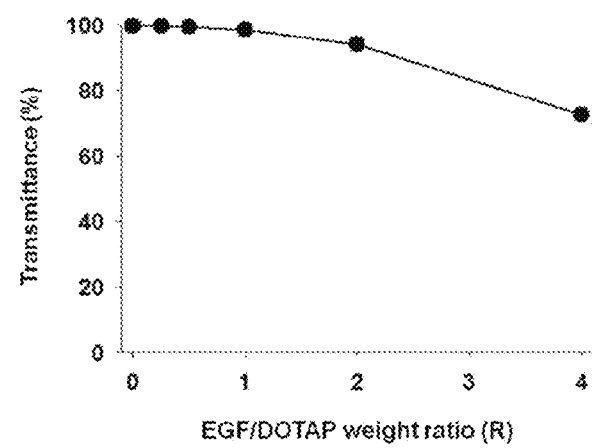
FIG. 3 shows the results of measuring the transmittance of EGF-DOTAP hybrid-type multi-lamellar nanostructures prepared according to one embodiment of the present invention.

As can be seen in FIG. 3, when the EGF/DOTAP weight ratio was 2 or less, the transmittance was maintained at a constant level, but when the weight ratio was more than 2, the transmittance decreased. Probably, this is because the amount of EGF that aggregates without being associated with the cationic empty unilamellar liposomes increases as the concentration of EGF increases.

Experimental Example 2

Evaluation of Encapsulation Efficiency of EGF in EGF-DOTAP Hybrid-Type Multi-Lamellar Nanostructures In order to measure the amount of EGF encapsulated in the EGF-DOTAP hybrid-type multi-lamellar nanostructures, the EGF-DOTAP hybrid-type multi-lamellar nanostructures (1 ml) prepared in Example 1.2 were centrifuged using an ultracentrifuge (200,000×g, 2 hrs, 4° C., Beckman) to separate non-encapsulated free EGF. The amount of the separated free EGF was measured using a micro BCA assay and an ELISA assay. The results of the measurement are shown in FIG. 4.

Figure 4:
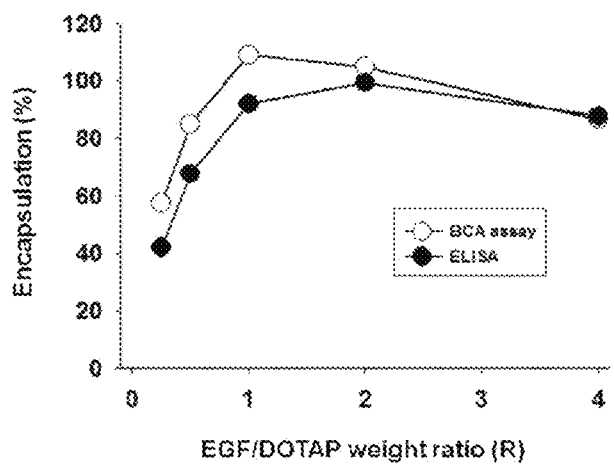
FIG. 4 shows the results of measuring the encapsulation rate of EGF-DOTAP hybrid-type multi-lamellar nanostructures prepared according to one embodiment of the present invention.

As can be seen in FIG. 4, a high encapsulation rate of 60% or more appeared at most of the EGF/DOTAP weight ratios with slight variations according to the method for quantifying EGF. Thus, it can be seen that the encapsulation efficiency in the structures according to the present invention is significantly higher than that those in conventional liposomes which are only 10-20%.

Experimental Example 3

Confirmation of Formation of Multi-Lamellar Structures of EGF-DOTAP Hybrid-Type Multi-Lamellar Nanostructures In order to confirm formation of the multi-lamellar structures of the EGF-DOTAP hybrid-type multi-lamellar nanostructures, observation was performed with cryo-TEM using a plunge-dipping method enabling a particulate material in an aqueous solution to be exactly observed. 4 μl of the EGF-DOTAP hybrid-type multi-lamellar nanostructures prepared in Example 1.2 were placed on a lacey grid so as to form a thin layer. The thin aqueous layer was maintained at a suitable temperature and a humidity of 97-99% so that the solvent would not evaporate, after which it was rapidly dropped into liquid ethane (about −170° C.) to obtain a unilamellar frozen sample. The frozen sample made as described above was observed with a transmission electron microscope (JEM-3011, JEOL Ltd.) at an accelerating voltage (300 kV), and the data was analyzed using Gatan Digital Micrograph program.

As shown in FIG. 5, it was shown that the multi-lamellar structures of the EGF-DOTAP hybrid-type multi-lamellar nanostructures were formed by electrostatic attraction between EGF and DOTAP.

Experimental Example 4

Examination of Stability of EGF-DOTAP Hybrid-Type Multi-Lamellar Nanostructures

In order to examine the stability of EGF protein by the structural change of EGF in the EGF-DOTAP hybrid-type multi-lamellar nanostructures, circular dichroism (CD) was measured in the range of 180-260 nm by use or the Jasco-815 CD spectropolarimeter (Jasco-815, Jasco. Inc.). The EGF-DOTAP hybrid-type multi-lamellar nanostructures prepared in Example 1.2 were placed and analyzed in a 0.5 mm path length cell. As a control, free EGF not trapped in the nanostructures was used. The structural change of EGF was examined at varying temperatures for 100 days. The CD data are shown in FIG. 6.

Figure 6:
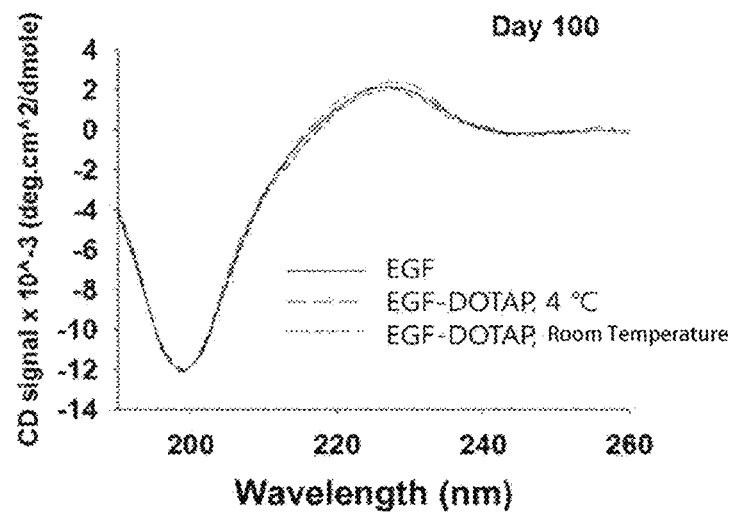
FIG. 6 shows the results of analyzing the stability of EGF-DOTAP hybrid-type multi-lamellar nanostructures prepared according to one embodiment of the present invention.

As can be seen in FIG. 6, the EGF-DOTAP hybrid-type multi-lamellar nanostructures stored at 4° C. (EGF-DOTAP, 4° C.) and the EGF-DOTAP hybrid-type multi-lamellar nanostructures stored at normal temperature (EGF-DOTAP, normal temperature) did not undergo a great physical change, compared to the control (EGF).

Experimental Example 5

Examination of Skin Permeability of EGF-DOTAP Hybrid-Type Multi-Lamellar Nanostructures To examine the skin permeability of the EGF-DOTAP hybrid-type multi-lamellar nanostructures, nude mice (SKH-1 Hairless, 5 week old, Orientbio, Korea) were used. A PDMS mold (diameter: 0.8 cm; height: 0.5 cm) was fixed to the back of each mouse, and 50 ml of a sample obtained by reacting a fluorescent (FITC) with EGF, DOTAP or EGF-DOTAP hybrid-type multi-lamellar nanostructures prepared in Example 1.2 was loaded in the PDMS mold and allowed to react with the mouse skin for 1 hour. The skin isolated from the mouse was sectioned with a cryostat microtome (Leica CM1850, Leica Microsystems), and then observed with a fluorescence microscope (Leica DMI 3000 B, Leica Microsystems).

Figure 7A:
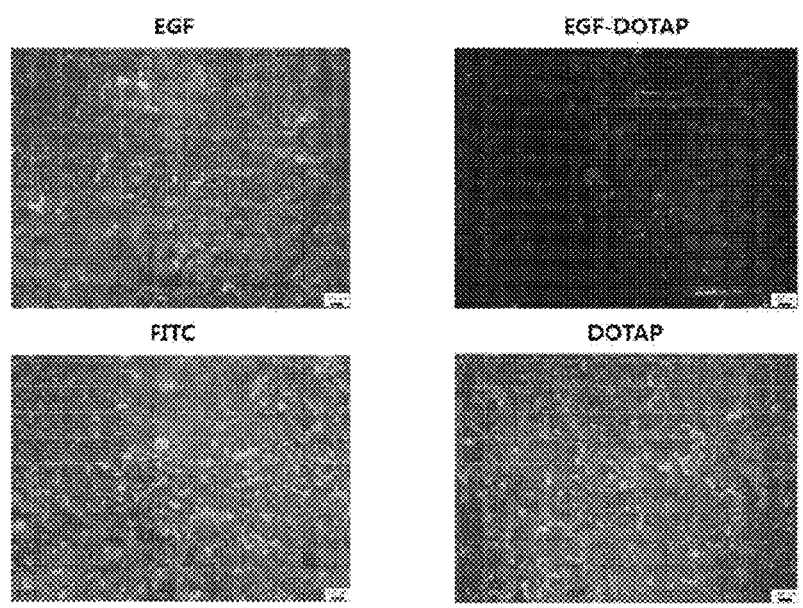
FIG. 7 shows the results of measuring the skin permeation Properties of EGF-DOTAP hybrid-type multi-lamellar nanostructures prepared according to one embodiment of the present invention (FIG. 7a: skin surface.
FIG. 7b: skin section).

As shown in FIG. 7a, it was observed that EGF or DOTAP alone was deposited on the skin surface without penetrating the epidermis, but the EGF-DOTAP hybrid-type multi-lamellar nanostructures did not remain on the skin surface.

Figure 7B:
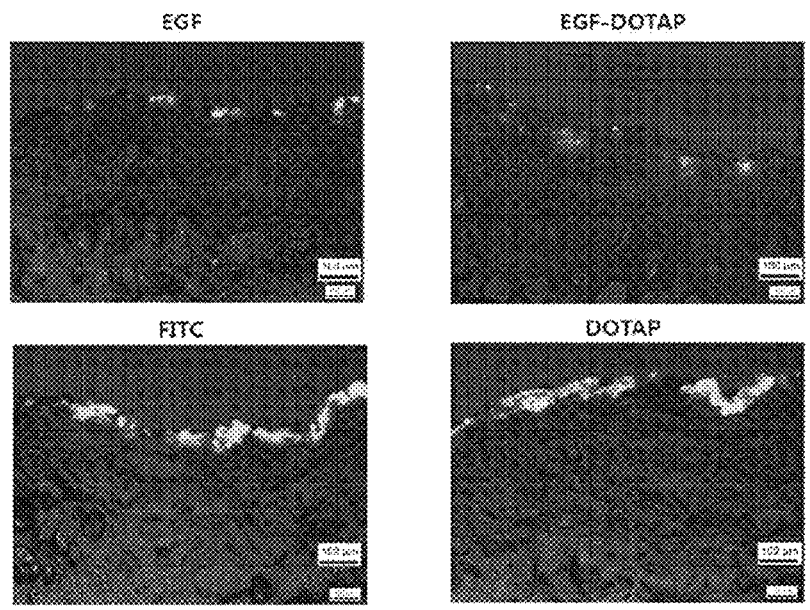

Furthermore, as shown in FIG. 7b, the observation of the skin sections obtained using the microtome indicated that the EGF-DOTAP hybrid-type multi-lamellar nanostructures permeated from the epidermis of the skin to the dermis.

Based on the results of the above experimental examples, formulation examples of cosmetic compositions containing the EGF-DOTAP hybrid-type multi-lamellar nanostructures of the present invention will now be described. However, the compositions of the present invention are not limited to these formulation examples.

Formulation Example 1

Skin Lotion

A skin lotion having the composition shown in Table 2 below was prepared according to a conventional method.

TABLE 2

| Composition of skin lotion | |
|---|---|
| Components | Contents (parts by weight) |
| EGF-DOTAP hybrid-type multi-lamellar nanostructures | 0.5 |
| 1,3-butylene glycol | 6.0 |
| Glycerin | 4.0 |
| Oleyl alcohol | 0.1 |
| Polysorbate 20 | 0.5 |
| Ethanol | 15.0 |
| Benzophenone-9 | 0.05 |
| Fragrance and preservative | q.s. |
| Purified water | to 100 |

Formulation Example 2

Milk Lotion

A milk lotion having the composition shown in Table 3 below was prepared according to a conventional method.

TABLE 3

| Composition of milk lotion | |
|---|---|
| Components | Contents (parts by weight) |
| EGF-DOTAP hybrid-type multi-lamellar nanostructures | 1.0 |
| Propylene glycol | 6.0 |
| Glycerin | 4.0 |
| Triethanolamine | 1.2 |
| Tocopheryl acetate | 3.0 |
| Liquid paraffin | 5.0 |
| squalane | 3.0 |
| Macadamia nut oil | 2.0 |
| Polysorbate 60 | 1.5 |
| Sorbitan sesquioleate | 1.0 |
| Carboxyvinyl polymer | 1.0 |
| BHT | 0.01 |
| EDTA-2Na | 0.01 |
| Fragrance and preservative | q.s. |
| Purified water | to 100 |

Formulation Example 3

Essence

An essence having the composition shown in Table 4 below was prepared according to a conventional method.

TABLE 4

Composition of essence

| Components | Contents (parts by weight) |
| --- | --- |
| EGF-DOTAP hybrid-type multi-lamellar nanostructures | 2.0 |
| Sitosterol | 1.7 |
| Polyglyceryl 2-oleate | 1.5 |
| Ceramide | 0.7 |
| Ceteareth-4 | 1.2 |
| Dicetyl phosphate | 0.4 |
| Concentrated glycerin | 0.5 |
| Carboxyvinyl polymer | 0.2 |
| Xanthan gum | 0.2 |
| Fragrance and preservative | q.s. |
| Purified water | To 100 |

Formulation Example 4

Nourishing Cream

A nourishing cream having the composition shown in Table 5 below was prepared according to a conventional method.

TABLE 5

Composition of nourishing cream

| Components | Contents (parts by weight) |
| --- | --- |
| EGF-DOTAP hybrid type multi-lamellar nanostructures | 2.0 |
| Cetostearyl alcohol | 2.0 |
| Glyceryl stearate | 1.5 |
| Trioctanoin | 5.0 |
| Polysorbate 60 | 1.2 |
| Sorbitan stearate | 0.5 |
| Squalane | 5.0 |
| Liquid paraffin | 3.0 |
| Cyclomethicone | 3.0 |
| BHT | 0.05 |
| Delta-tocopherol | 0.2 |
| Concentrated glycerin | 4.0 |
| 1,3-butylene glycol | 2.0 |
| Xanthan gum | 0.1 |
| EDTA-2Na | 0.05 |
| Fragrance and preservative | q.s. |
| Purified water | to 100 |

Formulation Example 5

Pack

A pack cream having the composition shown in Table 6 below was prepared according to a conventional method.

TABLE 6

Composition of pack

| Components | Contents (parts by weight) |
| --- | --- |
| EGF-DOTAP hybrid-type multi-lamellar nanostructures | 1.0 |
| Propylene glycol | 2.0 |
| Glycerin | 4.0 |
| Carboxyvinyl polymer | 0.3 |
| Ethanol | 7.0 |
| PEG-40 hydrogenated castor oil | 0.8 |
| Triethanolamine | 0.3 |
| BHT | 0.01 |
| EDTA-2Na | 0.01 |
| Fragrance and preservative | q.s. |
| Purified water | to 100 |

The invention claimed is:

1. A cosmetic method comprising:
applying a plurality of nanostructures to skin, each nanostructure of the plurality of nanostructures being dispersed in a cosmetic composition and comprising:
a unilamellar liposome having an empty internal space composed of a cationic lipid bilayer comprising 1,2-dioleoyl-3-trimethylammonium-propane;
one or more cationic lipid bilayers covering the unilamellar liposome; and
encapsulated epidermal growth factor between the cationic lipid bilayers;
wherein the nanostructure has a series of substantially spherical shells formed of lipid bilayers interspersed with aqueous layers with a particle size of 100-200 nm and a zeta potential of +1 to 40 mV;
non-encapsulated epidermal growth factor wherein the encapsulated epidermal growth factor is 60% or more of total epidermal growth factor that is composed of the encapsulated epidermal growth factor and the non-encapsulated epidermal growth factor; and
wherein a weight ratio (w/w) of the total epidermal growth factor: the cationic lipid is 0.001 to 2: 1; and
allowing sufficient time for the plurality of nanostructures to permeate from the cosmetic composition to dermis of the skin.

2. The cosmetic method of claim 1 wherein the cosmetic composition is one of a skin softener, an emulsion, a nourishing cream, a pack, or a beauty liquid, essence.

3. The cosmetic method of claim 1 wherein the cosmetic composition contains one or more of oils, water, surfactants, moisturizing agents, lower alcohols, thickeners, chelating agents, pigments, preservatives, or fragrances.

* * * * *